United States Patent [19]

Mori

[11] Patent Number: 4,936,668
[45] Date of Patent: Jun. 26, 1990

[54] LIGHT RADIATOR

[76] Inventor: Kei Mori, 3-16-3-501 Kaminoge, Setagaya-ku, Tokyo, Japan

[21] Appl. No.: 371,468

[22] Filed: Jun. 26, 1989

[30] Foreign Application Priority Data

Nov. 25, 1988 [JP] Japan .................................. 63-297550

[51] Int. Cl.⁵ .............................................. G02B 6/00
[52] U.S. Cl. .................. 350/96.15; 350/96.10; 350/96.20
[58] Field of Search ............... 350/96.15, 96.10, 96.20, 350/96.29

[56] References Cited

U.S. PATENT DOCUMENTS

| | | | |
|---|---|---|---|
| 4,389,085 | 6/1983 | Mori | 350/96.10 |
| 4,459,642 | 7/1984 | Mori | 350/96.20 X |
| 4,460,243 | 7/1984 | Strait, Jr. | 350/96.20 X |
| 4,461,538 | 7/1984 | Breed, III et al. | 350/96.20 |
| 4,678,279 | 7/1987 | Mori | 350/96.29 X |
| 4,732,443 | 3/1988 | Mori | 350/96.10 |
| 4,770,484 | 9/1988 | Mori | 350/96.15 |

Primary Examiner—John D. Lee
Assistant Examiner—Phan T. Heartney
Attorney, Agent, or Firm—Jordan and Hamburg

[57] ABSTRACT

A light radiator is described which is capable of being threadably attached to the light-emitting end of a fiber optic cable to radiate light rays transmitted therethrough. The light-guide rod has a thread at a circumference of its one end in order to be threadably connected to the light-emitting end of the fiber optic cable and the light-guide rod has a spiral groove at its circumference. The spiral groove gradually getting deeper as it approaches the rod's tip in order to diffusively radiate the light therefrom.

16 Claims, 3 Drawing Sheets

LIGHT RADIATOR

BACKGROUND OF THE INVENTION

The present invention relates to a light radiator and relates more particularly to a light radiator for receiving light transmitted through a fiber optic cable and for radiating the same in such a way as to get a desired light distribution.

The present applicant has previously proposed various methods and systems to focus solar rays or artificial light rays by using lenses or the like to guide the focused light rays into a fiber optic cable and to transmit them to any place where the light is needed for illumination or for other purposes as for example to promote the cultivation of plants; for the propagation of chlorella; for giving beauty treatments through sunbathing; for giving medical treatments through light radiation etc. If light rays are emitted from the cut-off end of a fiber optic cable, they can be radiated only within a small angle of radiation of about 46° since focused light rays have a certain directivity. Therefore, desirable light radiation for the above-mentioned purposes may not be obtained if light is directly emitted from the cut-off end of the fiber optic cable. In order to solve this problem, the present applicant has also proposed various kinds of light radiators which can effectively diffuse the light rays transmitted through a fiber optic cable and to radiate the same to any desired space.

A light radiator previously proposed by the present applicant comprises, for example, a light guide and a groove that is spirally cut on the surface of the light guide.

The light introduced into the light guide is reflected on a grooved portion thereof and effectively radiated therefrom for use as illumination and for other intended purposes.

In this case, if the spiral groove is made in such a way that the spiral pitch gradually becomes narrow or the groove itself gradually deepens in the direction of the light then a substantially uniform radiation of the light from the whole body of the light guide may be realized.

SUMMARY OF THE INVENTION

It is an object of the present invention to provide a light radiator which is capable of receiving the light transmitted through a fiber optic cable and of radiating the same with the desired light distribution characteristics.

It is another object of the present invention to provide a light radiator which can be effectively connected to a fiber optic cable and, more particularly, to provide a low cost, simply constructed light radiator.

DESCRIPTION OF THE PREFERRED EMBODIMENTS

Figure 1:
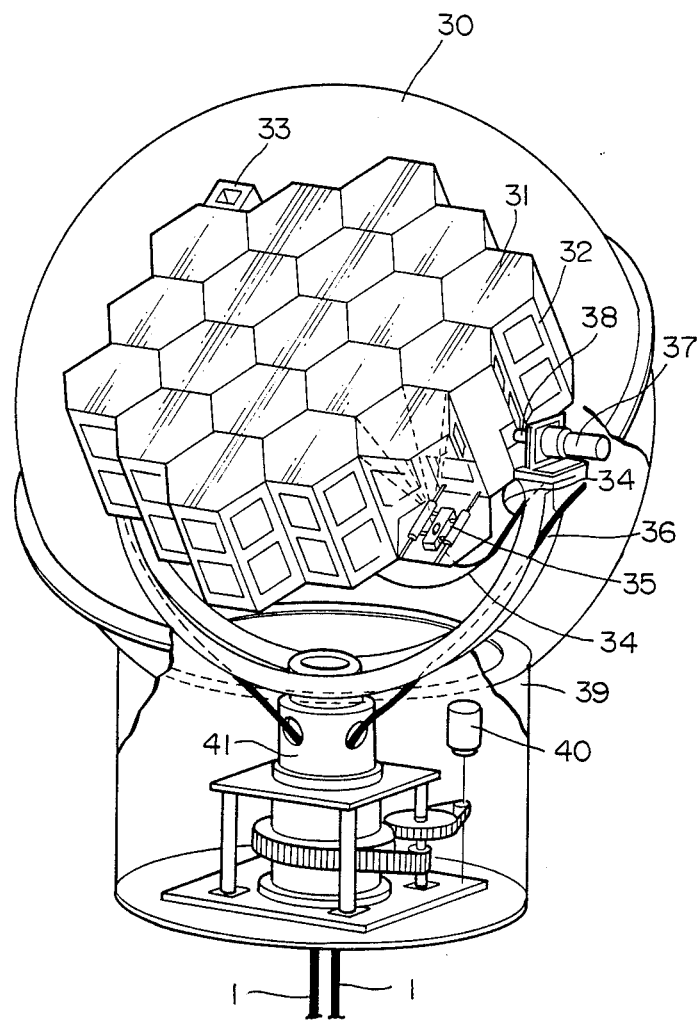
FIG. 1 is a view illustrating a solar ray collecting device which serves as an example for a system for introducing light rays into a fiber optic cable.

FIG. 1 is a construction view for illustrating, by way of example, a solar ray collecting device for guiding the sunlight into a fiber optic cable. In FIG. 1, numeral 30 is a transparent capsule, 31 is a Fresnel lens, 32 is a lens holder, 33 is a solar position sensor, 34 is a fiber optic cable consisting of a large number of optical fibers having light-receiving end surfaces set on the focal plane of the Fresnel lens system, 35 is a holder of the fiber optic cable, 36 is an arm, 37 is a pulse motor, 38 is a horizontal rotary shaft to be driven by the pulse motor 37, 39 is a base for supporting the protective capsule 30, 40 is a pulse motor and 41 is a vertical rotary shaft to be driven by the pulse motor 40.

The direction of the sun is detected by means of the solar position sensor 33 and its detection signal controls the pulse motors 37 and 38 of the horizontal and vertical rotation shafts 38 and 39 respectively so as to always direct the solar position sensor toward the sun, and the sunlight focused by the lens 31 is guided into the fiber optic cable 34 through its end-surface set at the focal point of the lens. All of the fiber optic cable 34, separately placed at each lens, are bundled together in a fiber optic cable 1, the free end of which is led to any place where light radiation is needed for the afore-mentioned purposes.

Figure 2:
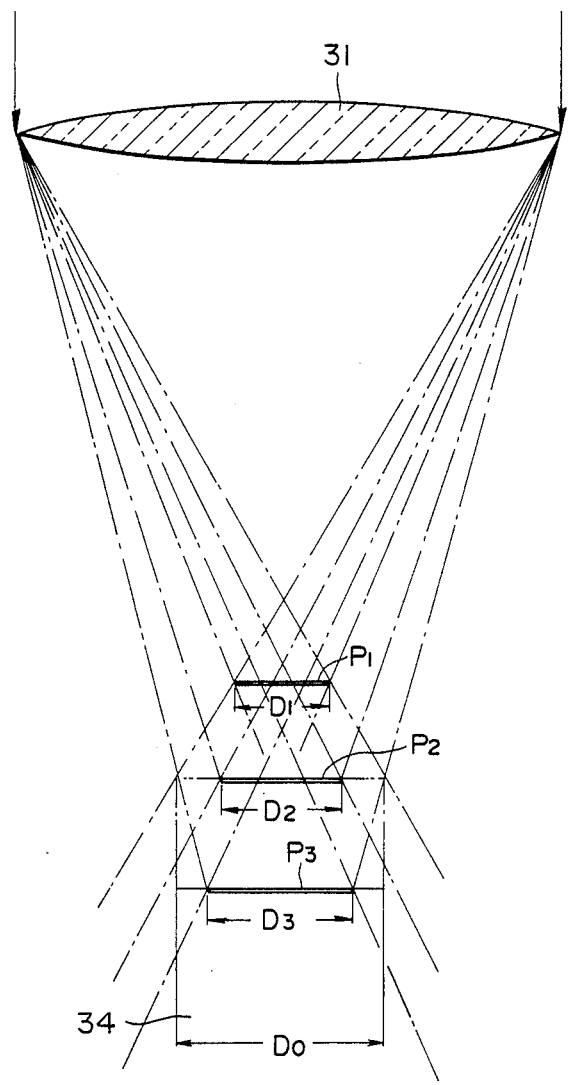
FIG. 2 is a view for explaining a practical example for introducing light rays into a fiber optic cable.
Figure 3:
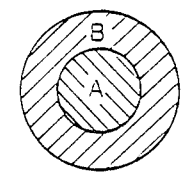
FIG. 3 shows an example of a solar image produced through a lens.

FIG. 2 is a view for explaining how to guide the solar rays collected by the above-mentioned lens 31 into the light guides. In FIG. 2, 31 is a Fresnel lens or the like and 34 is a fiber optic cable which receives the sunlight focused by the lens 31 and which transmits the same to any desired place. In case of focusing the sunlight through the lens system, the solar image has a central portion A, as shown in FIG. 3, consisting of almost white light and a circumferential portion B containing therein a large amount of the light components having wave-lengths corresponding to the focal point of the lens system. Namely, in the case of focusing sunlight through the lens system, the focal point and the size of the solar image will vary in accordance with the component wave-lengths of the light. For instance, the blue color light having a short wave-length makes a solar image of diameter D1 at position P1. Furthermore, the green color light makes a solar image of diameter D2 at position P2 and the red color light makes a solar image of diameter D3 at position P3. Consequently, as shown in FIG. 2, when the light-receiving end-surfaces of the light guides are set at position P1, it is possible to collect the sunlight containing plenty of the blue color components at the circumferential portion thereof. When the light-receiving end-surfaces of the light guides are set at position P2, it is possible to collect the sunlight containing plenty of the green color components at the circumferential portion thereof. When the light-receiving end-surfaces of the light guides are set at position P3 it is possible to collect the sunlight containing plenty of red color components at the circumferential portion thereof. In each case, the diameter of the fiber optic cable 34 can be selected in accordance with the light components to be collected. For instance, the required diameters of fiber optic cables are D1, D2 and D3, respectively, depending on the colors of the light rays to be stressed, i.e. the blue, green and red colors. In such a way, the required amount of light guides can be saved and thereby the sunlight containing therein plenty of desired color components can be collected most effectively.

And further, as shown in FIG. 2, if the diameter of the light-receiving end-surface of the light guide is enlarged to D0, it may be possible to collect visible light containing therein all of its wavelength components. The fiber optic cable 34 may be pre-set at the focal point of the lens system in the manufacturing process or they may be left in a adjustable condition in the axial direction of the lens system to allow the user to adjust and fix said light guides depending upon the desired color of the light to be obtained. By selecting the wave-length of the light components to be introduced into the fiber optic cable, it becomes possible to use the light radiating system more effectively for various purposes. The above-mentioned example relates to the device for introducing the solar rays into the fiber optic cable. However, it is also possible to introduce artificial light into the fiber optic cable.

Figure 4:
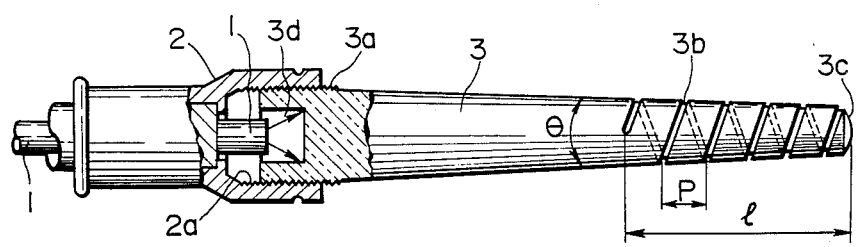
FIGS. 4 to 6 are construction views for showing the respective light radiators embodied in the present invention.
Figure 5:
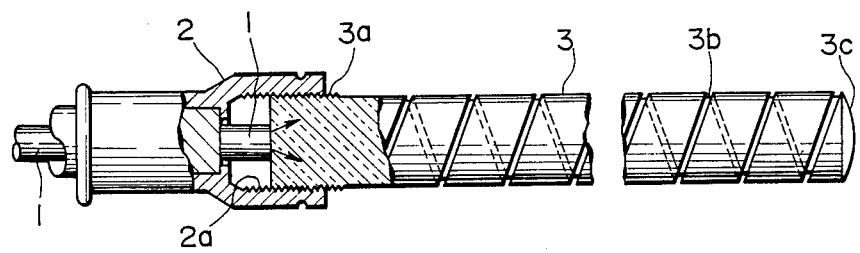
Figure 6:
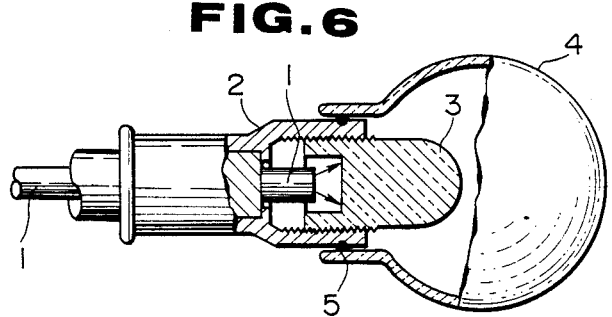

FIGS. 4 to 6 are construction views for explaining the respective light radiation devices embodying the present invention. In FIGS. 4, 5 and 6, numeral 1 is a fiber optic cable (which corresponds to the fiber optic cable 1 or 34 shown in FIG. 1), 2 is a connector attached to the light-emitting end of said fiber optic cable; 3 is a light radiator comprising light guiding rod made of acrylic resin or the like and 4 is a transparent or semitransparent cover member. As shown in FIG. 4, the connector 2 has an inner thread 2a at least at its open end portion and the radiator 3 has at its one end an outer thread 3a, by which said radiator is connected to said connector's thread 2a. The radiator can be used when its threaded portion 3a engages the connector's threaded portion 2a.

In the embodiment shown in FIG. 4, the light radiator, comprising a tapered light-guide rod 3 has a thread 3a at the circumference of one end of a large diameter and a spiral groove 3b at its tapered portion. The spiral groove 3b can be selected for its length l and pitch P. Accordingly, any desired light distribution characteristics may be obtained by selecting a tapered angle θ, a spiral pitch P and the proper length l of the spiral groove. Specifically, if the tapered light guide rod 3 has no spiral groove 3b, light rays introduced into the rod are emitted mainly from the tip portion 3c of the rod. On the other hand, the light-guide rod has a spiral groove 3b allowing it to emit the light rays from a wide portion l including the tip. For example, in the case when the light radiator is inserted into an opening of the human body such as the mouth, nose or anus to radiate light rays for giving medical treatments therein, the light can be radiated not only forward from the tip portion but also sideways from the cylindrical surface of the end portion of its light-guide rod. Particularly, the radiator may be easily put into the anus to administer the medical treatment more effectively.

FIG. 5 is a view for explaining another embodiment of a light radiator according to the present invention. In FIG. 5, the light radiator comprises a cylindrical light-guide rod with a circumferential spiral groove 3b which is constructed in such a way that its depth becomes deeper or its spiral pitch becomes smaller as the groove gets nearer to the rod's tip 3c. Such a light radiator can radiate the light evenly from the grooved portion of its rod and therefore can be used as a linear light source.

FIG. 6 is a view illustrating a further embodiment of the present invention. In FIG. 6, the light radiator has a light-guide rod 3 with a semi-circular head for emitting light therefrom. Such a design for the light-guide rod makes it possible to provide a low cost light radiator since the necessity for cutting a spiral groove on the rod's body surface is eliminated. The light radiator shown in FIG. 6 is provided with a transparent or semitransparent cover member 4 which can be removably fitted onto a connector 2 to cover the light radiator. It is of course possible to provide the light radiators shown in FIG. 4 and 5 with a cover member similar to that shown in FIG. 6.

The advantage of attaching the cover member 4 to the light radiator is to increase the effectiveness of scattering light when using the light radiator in water and also to make the light softer by decreasing its brightness. The cover member 4 may be threadably attached to the connector 2. As shown in FIG. 6, it is also possible to put an O-ring 5 on the connector and then to simply fit the cover member 4 thereto by using the elastic deformation of said ring. Furthermore, in the light radiator shown in FIG. 4, the light emitted from the fiber optic cable 1 enters into the light-guide rod through a clearance 3d provided at the light-receiving end of the rod. On the other hand, as shown in FIG. 5, it is also possible to closely place or attach the light-receiving end of the light-guide rod 3 to the light-emitting end of the fiber optic cable.

I claim:

1. A light radiating device comprising a fiber optic cable means for transmitting light rays, said cable means having a longitudinal end portion terminating at a light-emitting end, a connector means attached to said longitudinal end portion, a light radiator made of a solid material and having a light-receiving end face, thread means on said connector means and on said light radiator for threadedly connecting said light radiator to said connector means at a position such that said light-receiving end face receives light rays remitted from said light-emitting end, said light radiator having a first portion on which said threads are formed and a second portion having a conical configuration, a spiral groove extending over at least a part of said conical portion such that the light-distribution characteristics of said conical portion of said light radiator are varied by varying the cone angle of said conical portion, varying the pitch of said spiral groove, and varying the area of said conical portion over which said spiral groove extends.

2. A light radiating device according to claim 1, wherein said light-receiving end face has a diameter greater than the diameter of said light-emitting end of said cable means.

3. A light radiating device according to claim 1, wherein said light radiator is made of acrylic resin.

4. A light radiating device comprising a fiber optic cable means for transmitting light rays, said cable means having a longitudinal end portion terminating at a light-emitting end, a connector means attached to said longitudinal end portion, a light radiator made of a solid material and having a light-receiving end face, thread means on said connector means on said light radiator for threadedly connecting said light radiator to said connector means at a position such that said light-receiving end face receives light rays emitted from said light-emitting end, said light radiator having one end portion on which said threads are formed, said light radiator having its other end portion formed with a hemispherical surface from which light rays are radiated.

5. A light radiating device according to claim 4, wherein said light-receiving end face has a diameter greater than the diameter of said light-emitting end of said cable means.

6. A light radiating device according to claim 4, wherein said light radiator is made of acrylic resin.

7. A light radiating device according to claim 4, further comprising cover means made of a transparent or semi-transparent material disposed about and spaced from said light radiator for changing the lighting characteristics of the light radiated from said light radiator.

8. A light radiating device according to claim 7, further comprising means attaching said cover means to said connector means.

9. A light radiating device comprising a fiber optic cable means for transmitting light rays, said cable means having a longitudinal end portion terminating at a light-emitting end, a light connector means attached to said end portion of said cable means and having an extending section which extends about said longitudinal end portion, said extending section having an internal cylindrical wall having internal threads thereon, said threaded internal cylindrical wall having a diameter greater than the diameter of said cable means, a light radiator made of a solid material and having a light-receiving end face, said light-receiving end face having a diameter greater than the diameter of said light-emitting end, and external thread means on said light radiator threadedly connecting said light radiator to said connector means at a position such that the light rays emitted from said light-emitting end of said cable pass into said light-receiving end face of said light radiator.

10. A light radiating device according to claim 9, wherein the smallest diameter of said light radiator anywhere along its longitudinal length is greater than the diameter of said light-emitting end of said cable means.

11. A light radiating device according to claim 9, wherein said light-receiving end face of said light radiator abuts said light-emitting end of said cable means.

12. A light radiating device according to claim 9, wherein said light-receiving end face of said light radiator is spaced from said light-emitting end of said cable means.

13. A light radiating device according to claim 9, wherein said extending section of said connector means extends beyond said light-emitting end of said cable means such that said internal threads also extend beyond said light-receiving end of said cable means.

14. A light radiating device according to claim 9, further comprising cover means made of a transparent or semi-transparent material disposed about and spaced from said light radiator for changing the lighting characteristics of the light radiated from said light radiator.

15. A light radiating device according to claim 14, further comprising attachment means for attaching said cover means to said connector means.

16. A light radiating device according to claim 9, wherein said light radiator has an end portion having a hemispherical surface from which light rays are radiated.

* * * * *